(12) United States Patent
Tsai et al.

(10) Patent No.: US 9,339,311 B1
(45) Date of Patent: May 17, 2016

(54) REAR-RETAINING STRUCTURE FOR DYNAMIC HIP SCREW

(71) Applicant: INTAI TECHNOLOGY CORPORATION, Taichung (TW)

(72) Inventors: Yung-Fang Tsai, Taichung (TW); Pei-Yuan Lee, Taichung (TW); Tsung-Chen Liu, Taichung (TW)

(73) Assignee: INTAI TECHNOLOGY CORPORATION, Taichung (TW)

( * ) Notice: Subject to any disclaimer, the term of this patent is extended or adjusted under 35 U.S.C. 154(b) by 0 days.

(21) Appl. No.: 14/551,620

(22) Filed: Nov. 24, 2014

(51) Int. Cl.
*A61B 17/74* (2006.01)
*A61B 17/72* (2006.01)

(52) U.S. Cl.
CPC .................. *A61B 17/72* (2013.01); *A61B 17/74* (2013.01)

(58) Field of Classification Search
CPC .................. A61B 17/74–17/748; A61B 17/72
USPC ..................................................... 606/65–66
See application file for complete search history.

(56) References Cited

U.S. PATENT DOCUMENTS

| | | | | |
|---|---|---|---|---|
| 5,041,116 A | * | 8/1991 | Wilson | 606/65 |
| 2002/0016595 A1 | * | 2/2002 | Michelson | 606/73 |

* cited by examiner

*Primary Examiner* — Nicholas Plionis
(74) *Attorney, Agent, or Firm* — Pai Patent & Trademark Law Firm; Chao-Chang David Pai

(57) ABSTRACT

A rear-retaining structure for dynamic hip screw (DHS) includes a retaining block and a positioning element. The dynamic hip screw comprises a lag screw, a sideplate, a sleeve with a higher orifice and a lower orifice, and a compression screw. The retaining block of the rear-retaining structure is attached to the sideplate of the dynamic hip screw by the positioning element. A stopper portion of the retaining block is located opposite to the lower orifice of the sleeve. The height of the highest point of the stopper portion in the lower orifice is in inverse proportion to the distance that the lag screw and the compression screw are allowed to slip back in the sleeve from an implant position to the lower orifice; namely, the higher the height of the highest point of the stopper portion is in the lower orifice, the smaller the distance for the slip back.

4 Claims, 9 Drawing Sheets

REAR-RETAINING STRUCTURE FOR DYNAMIC HIP SCREW

BACKGROUND OF THE INVENTION

1. Technical Field of the Invention

The present invention relates to a rear-retaining structure for dynamic hip screw (DHS). Especially, the present invention relates to a rear-retaining structure attached to a dynamic hip screw to stop the slip back or provide a limited macro-slip back of the lag screw and the compression screw of DHS.

2. Prior Arts

Clinically, proximal femoral fractures are common hip fractures. Internal fixation systems, such as DHS system and intramedullary fixation system are used in the current treatments. According to clinical implementations and researches, the therapeutic effect of DHS on the stable proximal femoral fracture has been affirmed.

As showed in FIG. 1, a typical DHS system comprises: a lag screw 1 to be inserted into the neck of the femur to fix the proximal end of a fracture; a sideplate 2 connected with a sleeve 3 set at the end of the lag screw 1 to fix the distal end of the fracture, the sleeve 3 being jacketed outside the lag screw 1 to support the lag screw 1 and prevent the rotation of the lag screw 1; and a compression screw 4 is locked into the lag screw 1 from the distal end of the sleeve 3. The tightening of the compression screw 4 will cause the lag screw 1 to lead the proximal end of the fracture outward and downward along the axis of the sleeve 3, because the supporting function of the sleeve 3. As a result, the ends of the fracture may be abutted to each other and pressed forces can be controlled to strengthen the component force perpendicular to the fracture line, thereby promoting the healing of the fracture.

In the healing process of proximal femur fracture, there are some factors causing a lot of stress to the lag screw 1 and compression screw 4 of DHS, including the component force for neck inversion, weight pressure, shear forces from muscle stretches, external rotation force of lower limb, cyclical stress-strain changes occurring at the fracture, and axial micro-movement bearing at the ends of fracture. The stress may cause the lag screw 1 and compression screw 4 to produce an excessive sliding back phenomenon (referred to as "slip back"), as showed in FIG. 2. The back-out of the lag screw 1 and compression screw 4 will lead to the shortening of bone torque (D1) and bone length (D2), which makes the length of the femur shorter after healing, and as a result the patients appear limp.

In some of the fracture healing process, allowing the lag screw 1 and compression screw 4 a limited sliding back, referred to as "macro slip back", will reduce the shear and stress concentration at the fracture, and prevent the downward shift of proximal fracture bone and the formation of collapse, inversion and slumping of femoral neck angle. But in other fracture healing process, it is also beneficial for fracture healing to fix the lag screw 1 and compression screw 4 for blocking their slip back. Therefore, whether the lag screw 1 and compression screw 4 should be in fixation or macro slip back depends on the individual condition of fractures.

SUMMARY OF INVENTION

The problem to be resolved in this invention is related to the excessive sliding back phenomenon of the lag screw and compression screw that occurred in conventional dynamic hip screw (DHS).

Accordingly, in one aspect, the present invention provides a rear-retaining structure for dynamic hip screw (DHS), which comprises a lag screw, a sideplate, a sleeve, and a compression screw, wherein the sleeve is obliquely connected to the top of the sideplate; the sleeve has an axial bore passing through the shaft axis of the sleeve, forming an upper orifice and a lower orifice at the two ends of the sleeve; the end of the lag screw enters the sleeve from the upper orifice, and the compression screw locks into the end of the lag screw from the lower orifice. The dynamic hip screw is to be fixed in the femoral neck fracture of the proximal femur.

The rear-retaining structure comprises a retaining block and a positioning element, wherein the positioning element mounts the retaining block on the surface of the sideplate at a position adjacent to the lower orifice of the sleeve; and the retaining block has a stopper portion opposite to the lower orifice. The height of the highest point of the stopper portion in the lower orifice is in inverse proportion to the distance that the lag screw and the compression screw are allowed to slip back in the sleeve from an implant position to the low orifice. In other words, the higher the height of the highest point of the stopper portion is in the lower orifice, the smaller the distance for the slip back.

In a first embodiment, the highest point of the stopper portion is located below the center of the lower orifice. There is a distance between the highest point of the stopper portion and the end surface of the compression screw at the implant site to allow the lag screw and the compression screw to slip back in the sleeve from the implant site to the low orifice. Preferably, the maximum range for slip back is controlled within about 10 mm.

In a further embodiment, the highest point of the stopper portion is located above the center of the lower orifice. There is no distance between the highest point of the stopper portion and the end surface of the compression screw at the implant site. The highest point of the stopper portion just withstands the end surface of the compression screw at the implant site to prevent the slip back of the lag screw and compression screw by fixing them at the implant position.

EFFECTS OF THE INVENTION

According to the present invention, after DHS is implanted into the position of a proximal femur fracture, the rear-retaining structure of the first embodiment allows the lag screw and compression screw of DHS for a limited macro slip back in response to the axial inching at the both sides of the fracture. The maximum range for slip back is controlled within about 10 mm. When the allowed macro-slip back distance is reached, the lag screw and compression screw will be stopped by the rear-retaining structure.

According to the rear-retaining structure of the present invention, the lag screw of DHS will allow a limited macro-slip back under a controlled condition. Therefore, a controlled fine axial inching at the both sides of the fracture is allowed to proceed for promoting callus formation and calcification, which can accelerate fracture healing. The rear-retaining structure of the present invention strengthens the dynamic compression effects of DHS to assist a faster healing of proximal femoral fracture.

According to the present invention, by the action of the rear-retaining structure, the lag screw and compression screw of DHS will allow a limited macro-slip back to fit the fine axial inching at the both sides of fracture. The axial inching will disperse the shear and stress, and reduce the probability of the collapse of the femoral neck angle caused by the downward shift of the proximal fracture fragment, and the cut out of lag screw to pierce from the femoral neck.

According to another embodiment of the present invention, after DHS is implanted into the position of a proximal femur fracture, the rear-retaining structure fixes the lag screw and compression screw of DHS at the implanted position to block the slip back of the lag screw and compression screw.

The rear-retaining structure of the present invention can not only stop the lag screw and compression screw, but also provide a function for supporting the lag screw and compression screw to reduce the bend or break of the lag screw caused by the concentrated stress.

Preferably, the rear-retaining structures according to the present invention are suitable for the fracture types 31-A1 to 31-C3 as defined in the AO Classification.

DETAILED DESCRIPTION OF THE INVENTION

Figure 1:
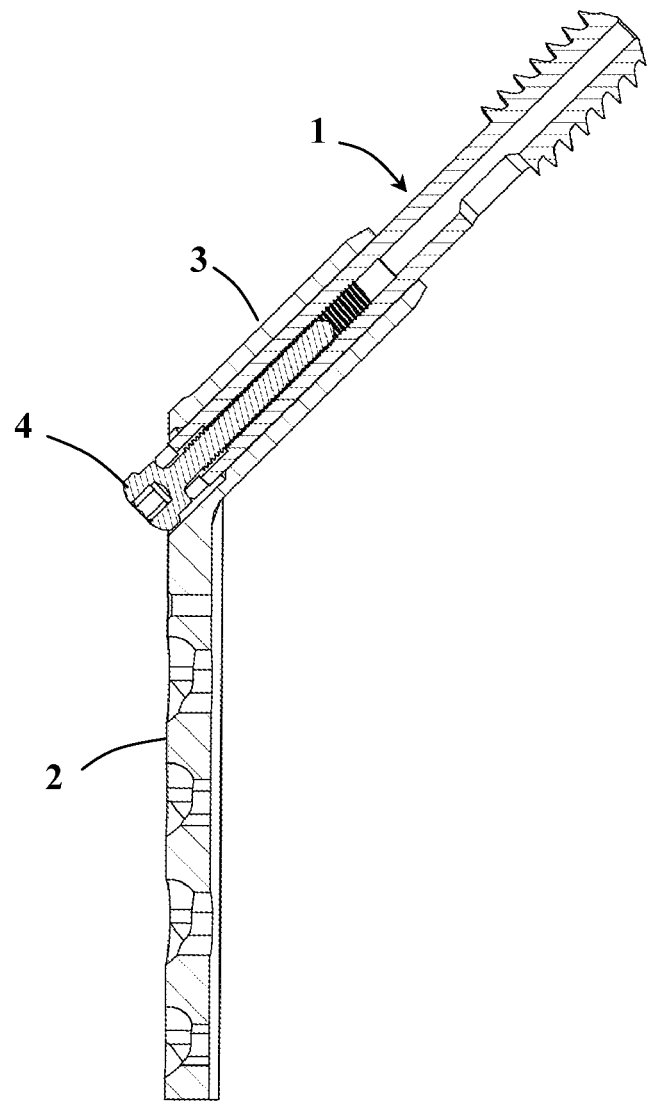
FIG. 1 shows a sectional view of a conventional dynamic hip screw (DHS).
Figure 2:
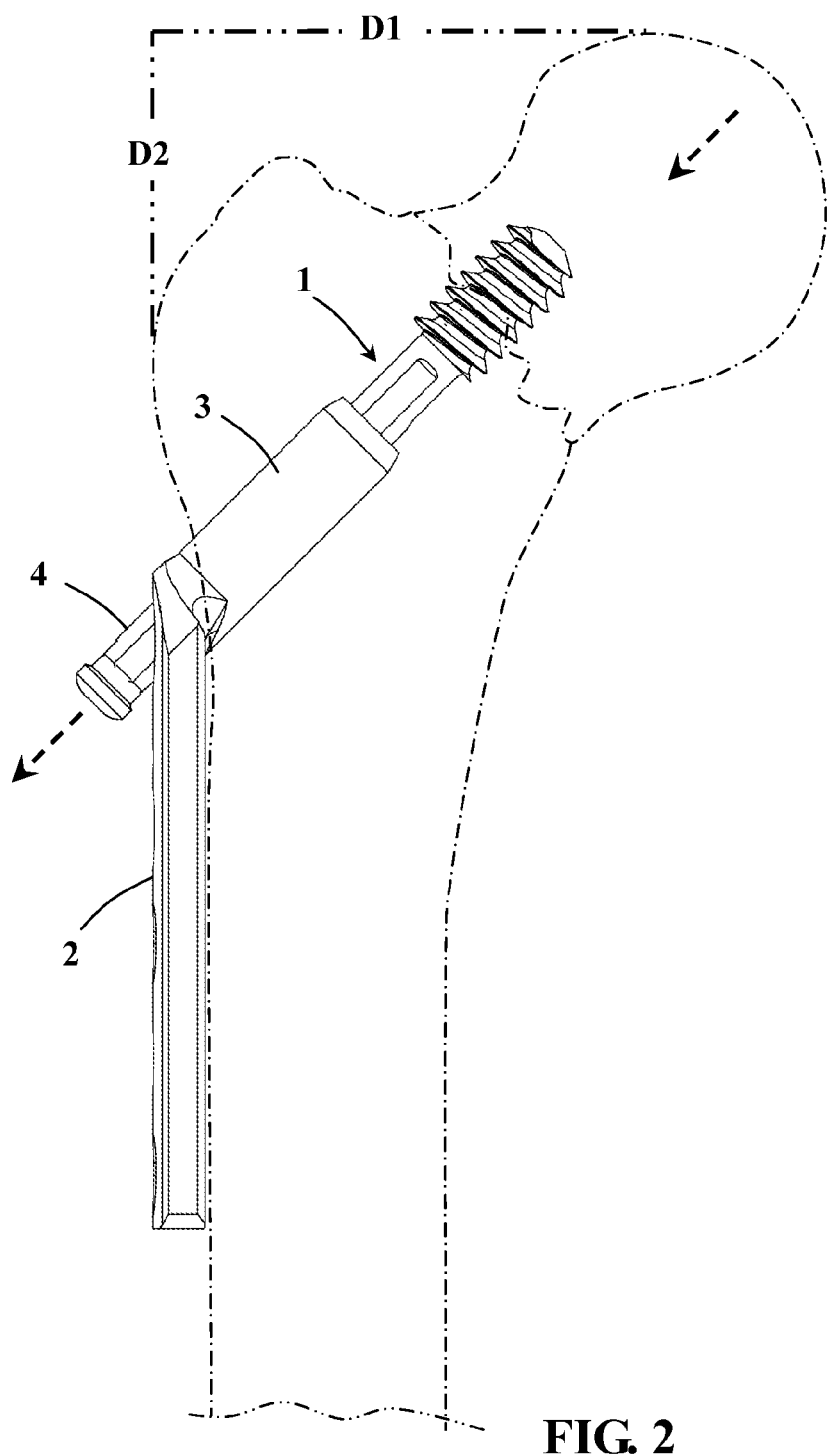
FIG. 2 is a schematic diagram showing the excessive sliding back out of the lag screw of a conventional DHS leading to the shortening of bone torque and bone length.

The other characteristics and advantages of the present invention will be further illustrated and described in the following examples. The examples described herein are used for illustrations, not for limiting the invention.

The elements or objects described in the following Embodiments are drawn according to the proportion, size, amount of deformation or amount of shift suitable for illustration, and might not to the scale of actual elements. Similar elements are represented by the same reference numerals.

FIGS. 3 to 9 describe a typical Dynamic Hip Screw (DHS) equipped with the rear-retaining structure in accordance with the present invention. A typical DHS system comprises a lag screw 1, a sideplate 2, a sleeve 3, and a compression screw 4. The sleeve 3 is connected to the top of the sideplate 2 via the first end 31 of the sleeve 3. The sideplate 2 is positioned vertically and the sleeve 3 is obliquely connected to the sideplate 2. The angle between the sleeve 3 and the sideplate 2 is maintained at about 110-150 degrees, and the second end 32 of the sleeve 3 is positioned higher than the first end 31. The sleeve 3 has an axial bore 5, which is set along the shaft axis of the sleeve 3. The axial bore 5 passes through the first end 31 of the sleeve 3, and therefore forms a lower orifice 7 at the first end 31 of the sleeve 3. Similarly, the axial bore 5 passes through the second end 32 of the sleeve 3, and forms an upper orifice 6 at the second end 32 of the sleeve 3. The end of the lag screw 1 is inserted into the femoral neck 90 to fix the proximal end of the fracture. The sleeve 3 is jacketed outside the lag screw 1 inserted through the upper orifice 6, thus supporting the lag screw 1 and to prevent the rotation of the lag screw 1.

The sideplate 2 is mounted outside the shaft of the femur 91 with bone screws (not showed). The compression screw 4 is inserted through the lower orifice 7 of the sleeve 3 and locked into the end of the lag screw 1. The tightening of the compression screw 4 will cause the lag screw 1 to lead the proximal end of the fracture outward and downward along the axis of the sleeve 3, resulting in the closing of the ends of the fracture onto each other, due to the functions of the sleeve 3 in supporting and preventing rotation of the lag screw 1. After confirming that the fracture has achieved the desired abutting, the lag screw 1 and compression screw 4 are positioned in the implant position, then a rear-retaining structure 8 is attached to the sideplate 2 of the DHS by way of screw locking As showed in FIGS. 3, 4, 7 and 8, the rear-retaining structure 8 comprises a retaining block 10 and a positioning element 30, wherein the retaining block 10 is mounted on the surface of the sideplate 2 at a position adjacent to the lower orifice 7 of the sleeve 3 by the positioning element 30. The retaining block 10 has a stopper portion 11 (in FIG. 3) or 21 (in FIG. 7) to stop the slip back of the lag screw 1 and compression screw 4.

Figure 5:
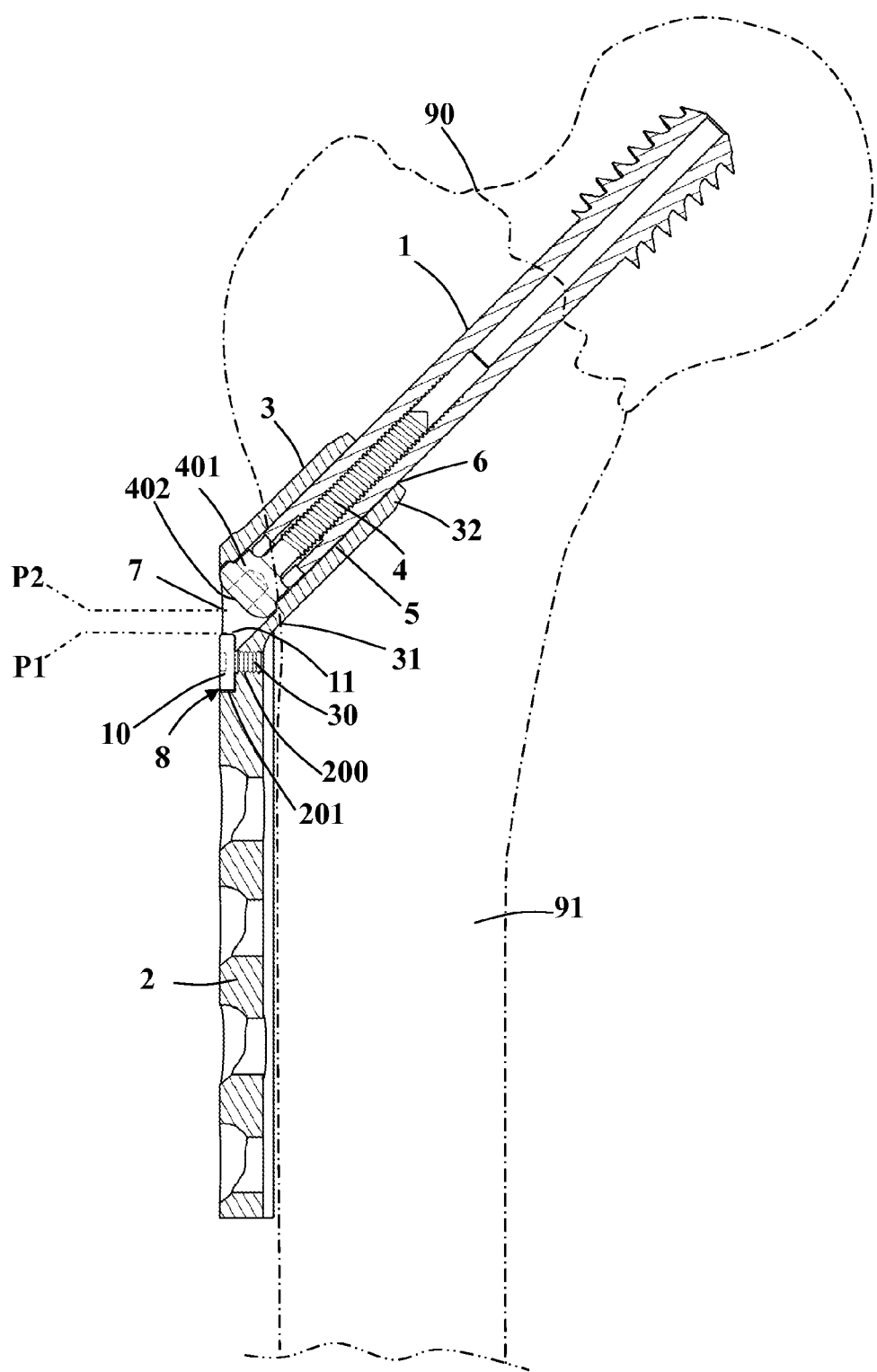
FIG. 5 is a sectional view of the assembly of a DHS with the rear-retaining structure of the first embodiment of the present invention.
Figure 9:
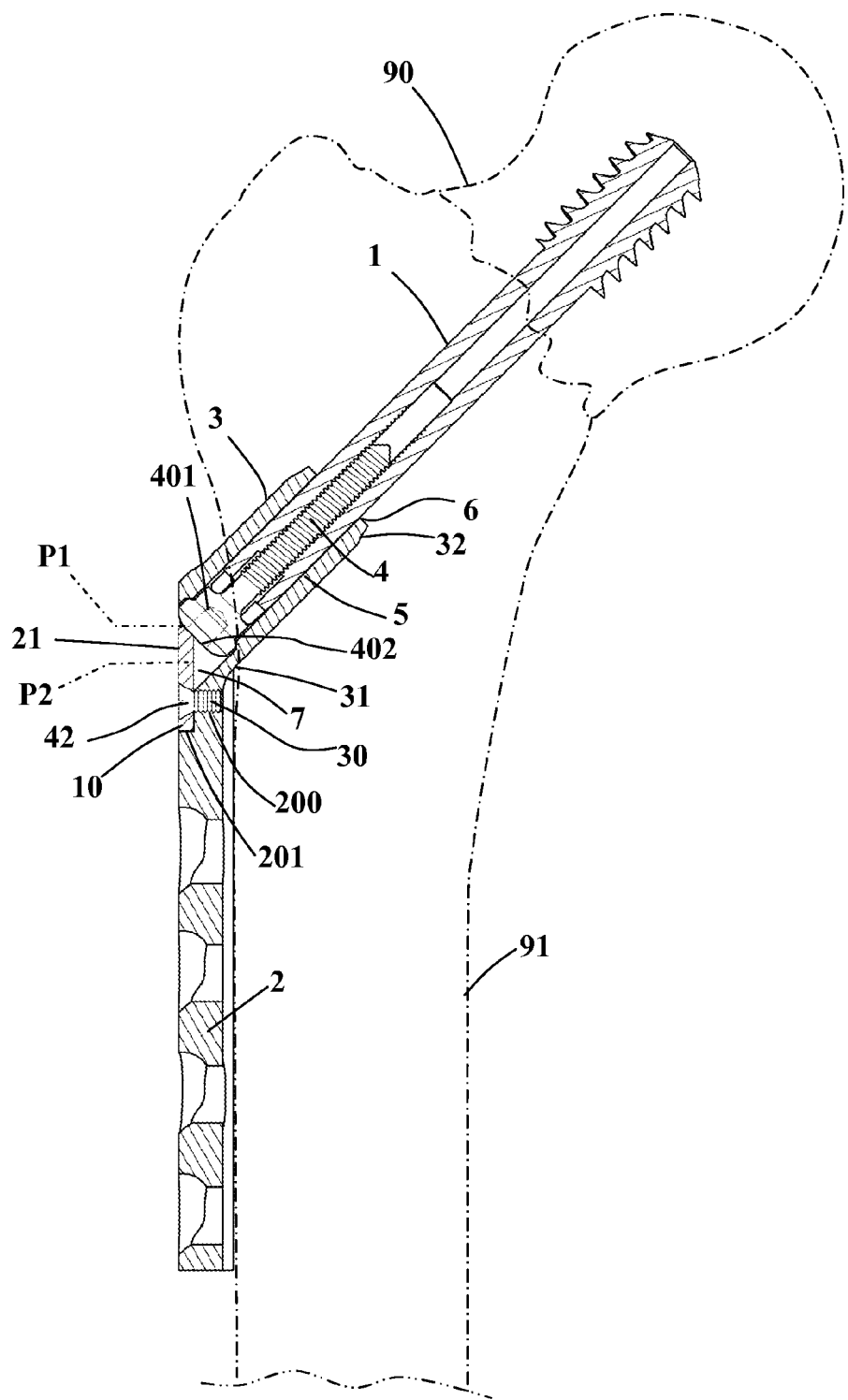
FIG. 9 is a sectional view showing the action of the rear-retaining structure of the second embodiment of the present invention to stop the lag screw and compression screw in a DHS.

As showed in FIGS. 5 and 9, the stopper portion 11 or 21 is located opposite to the lower orifice 7 of the sleeve 3. The straight slipping distance of the lag screw 1 and compression screw 4 toward the lower orifice 7 can be roughly determined from the height of the highest point P1 of the stopper portion 11 or 21 in the lower orifice 7. More specifically, the height of the highest point P1 of the stopper portion 11 or 21 in the lower orifice 7 is in inverse proportion to the distance that the lag screw 1 and the compression screw 4 are allowed to slip back in the sleeve 3 from an implant position toward the low orifice 7. Namely, the higher the height of the highest point P1 of the stopper portion 11 or 21 is in the lower orifice 7, the smaller the distance for the slip back. Preferably, the maximum range for slip back is controlled within about 10 mm.

Figure 6:
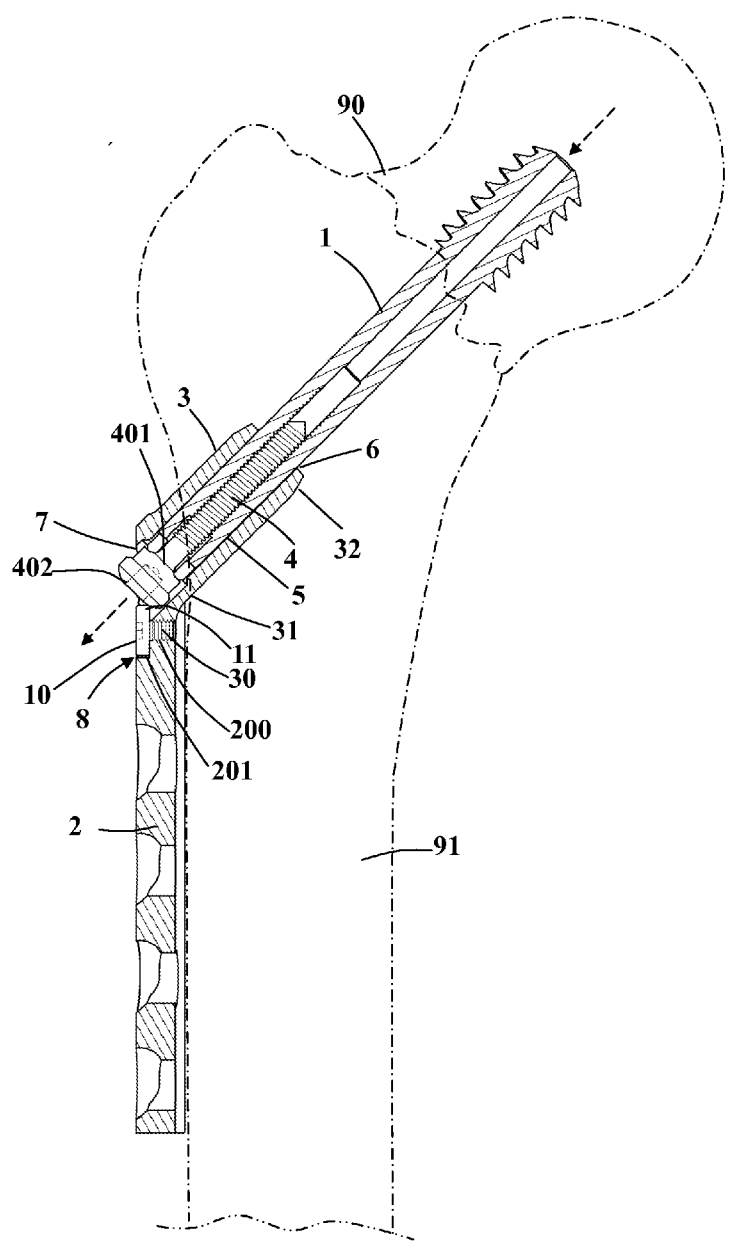
FIG. 6 is a sectional view showing the action of the rear-retaining structure of the first embodiment of the present invention to stop the lag screw and compression screw in a DHS.

As showed in FIGS. 5 and 6, the highest point P1 of the stopper portion 11 is located below the center point P2 of the lower orifice 7. There is a distance between the highest point p1 of the stopper portion 11 and the end surface 402 of the nail head 401 of the compression screw 4, allowing the lag screw 1 and the compression screw 4 to slip back in a direction from the implant site toward the lower orifice 7 as showed in FIG. 5. Preferably, the maximum range for slip back is controlled within about 10 mm, referred to as macro-slip back. When the allowed limit of macro-slip back distance is reached, the highest point p1 of the stopper portion 11 comes in contact with the end surface 402 of the nail head 401 of the compression screw 4. Consequently, the lag screw 1 and compression screw 4 will be stopped by the stopper portion 11, as showed in FIG. 6.

As showed in FIG. 9, the highest point P1 of the stopper portion 21 of the retaining block 10 is located above the center point P2 of the lower orifice 7. The highest point P1 of stopper portion 21 directly contacts the end surface 402 of the nail head 401 of the compression screw 4 at the implant site. As a result, the lag screw 1 and compression screw 4 are always kept in the implant position, and the lag screw 1 and compression screw 4 cannot slip back out.

Figure 3:
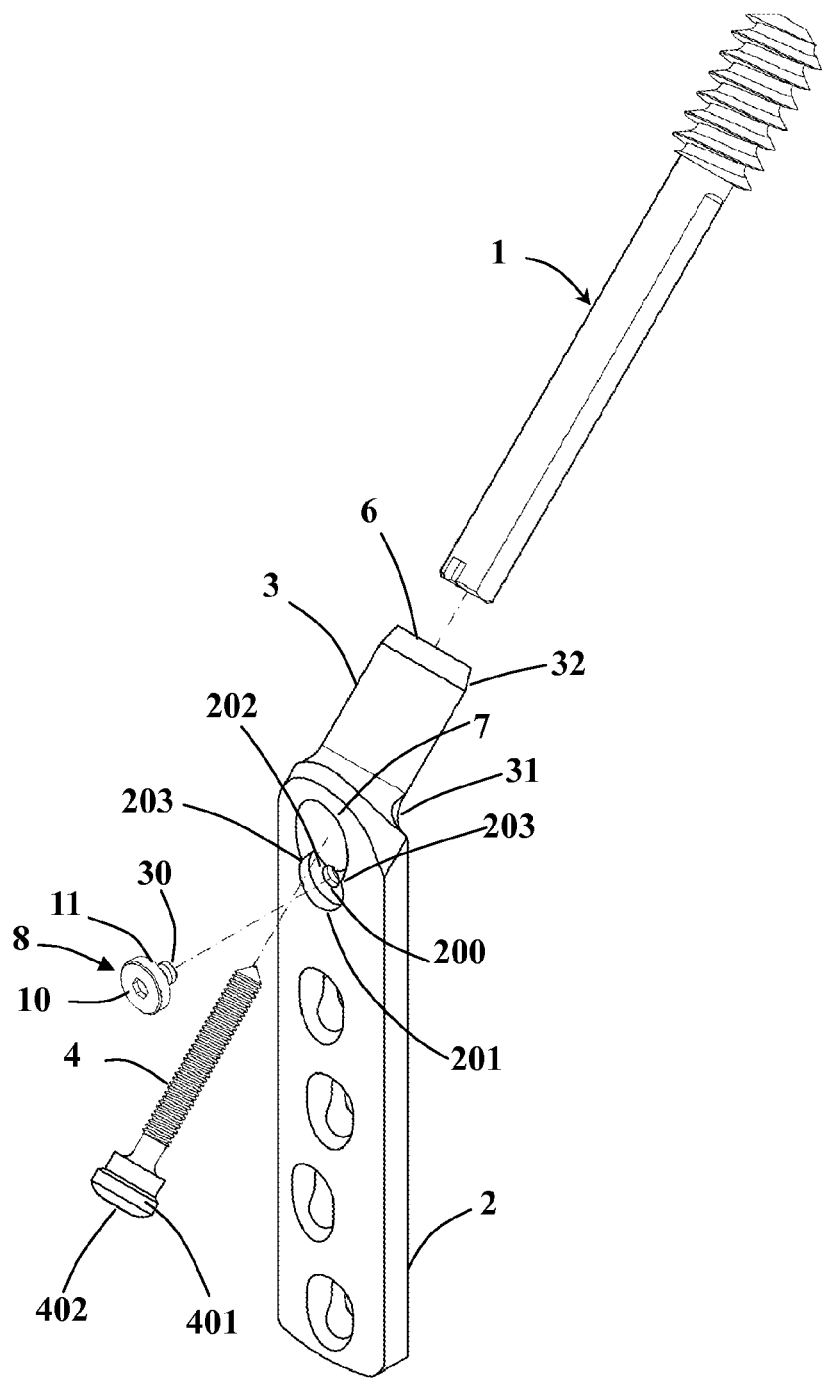
FIG. 3 is an exploded perspective view of a DHS and the rear-retaining structure of the first embodiment of the present invention.
Figure 4:
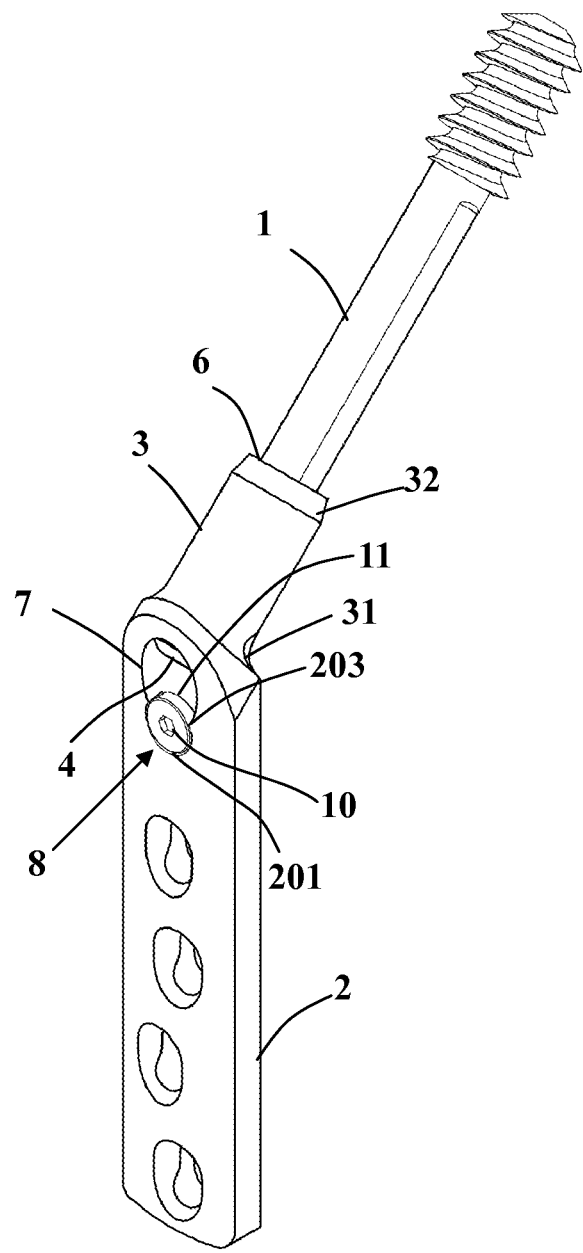
FIG. 4 is a three-dimensional view of the assembly of a DHS with the rear-retaining structure of the first embodiment of the present invention.

In the embodiment described in FIGS. 3 to 5, the retaining block 10 is presented as an integral (one-piece) structure. The positioning element 30 is integrally connected to the side of the retaining block 10. The retaining block 10 combined with the positioning element 30 forms a one-piece screw structure. The combination of the retaining block 10 and the positioning element 30 may also be in the embodiment showed in FIGS. 7 to 9. In that case, the positioning element 30 itself is a screw 41, and the retaining block 10 has a bore 12 for the screw 41 to pass through. The nail head 42 of the screw 41 will suppress and position the retaining block 10 onto the sideplate 2.

In the embodiment as described in FIGS. 3 to 5, the peripheral edge of the retaining block 10 comprises the stopper portion 11. A fixation hole 200 is set on the sideplate 2 at a position near the lower orifice 7 of the sleeve 3. The fixation hole 200 is a hole with a screw thread for locking the positioning element 30 into the fixation hole 200. The stopper portion 11 of the retaining block 10 is located opposite to the lower edge of the lower orifice 7, and the highest point P1 of the stopper portion 11 is located below the center point P2 of the lower orifice 7.

As showed in FIG. 5, the lag screw 1 and compression screw 4 are located in the implant position. There is a distance between the end surface 402 of the nail head 401 of the compression screw 4 and the highest point P1 of the stopper portion 11, which allows the lag screw 1 and the compression screw 4 to slip back out in response to the axial inching (or "micro-inching") at the both sides of the fracture during bone healing.

In the healing process of proximal femoral fractures, there are some factors causing a lot of stress to the lag screw 1 and the compression screw 4 of DHS, including the component force for neck inversion, weight pressure, shear forces from muscle stretches, external rotation force of lower limb, cyclical stress-strain changes occurring at the fracture, and axial micro-movement bearing at the ends of fracture. These factors will make the lag screw 1 slip back down along the sleeve 3. When the allowed limit of macro-slip back is reached, the nail head 401 of the compression screw 4 is stopped by the stopper portion 11 of the retaining block 10, as showed in FIG. 6. Therefore, the problem of excessive slip back as described in Prior Arts can be avoided in this way.

The allowance for the lag screw 1 and the compression screw 4 to produce a limited macro-slip back will allow the both sides of the fracture to proceed a controlled fine axial inching (referred micro-inching), which may promote callus formation and calcification, accelerate fracture healing, strengthen the dynamic compression effects of DHS to assist a faster healing of proximal femoral fracture, and will disperse the shear and stress to reduce the probability of the collapse of the femoral neck angle caused by the downward shift of the proximal fracture fragment and the cut out of lag screw to pierce from the femoral neck.

As showed in FIGS. 3 to 5, a container housing tank 201 is set on the surface of the sideplate 2 located below the lower orifice 7 of the sleeve 3, and a communicating part 202 is set between the lower orifice 7 and the container housing tank 201. The said fixation hole 200 is located in the slot base of the container housing tank 201. The retaining block 10 is locked in the container housing tank 201 by the positioning element 30, and the stopper portion 11 is located opposite to the lower edge of the lower orifice 7 through the communicating part 202. The advantage of setting the retaining block 10 in the container housing tank 201 is that the retaining block 10 will not protrude past the surface of the fixed plate 2, and the surface of the sideplate 2 can keep flat without bulges.

Figure 7:
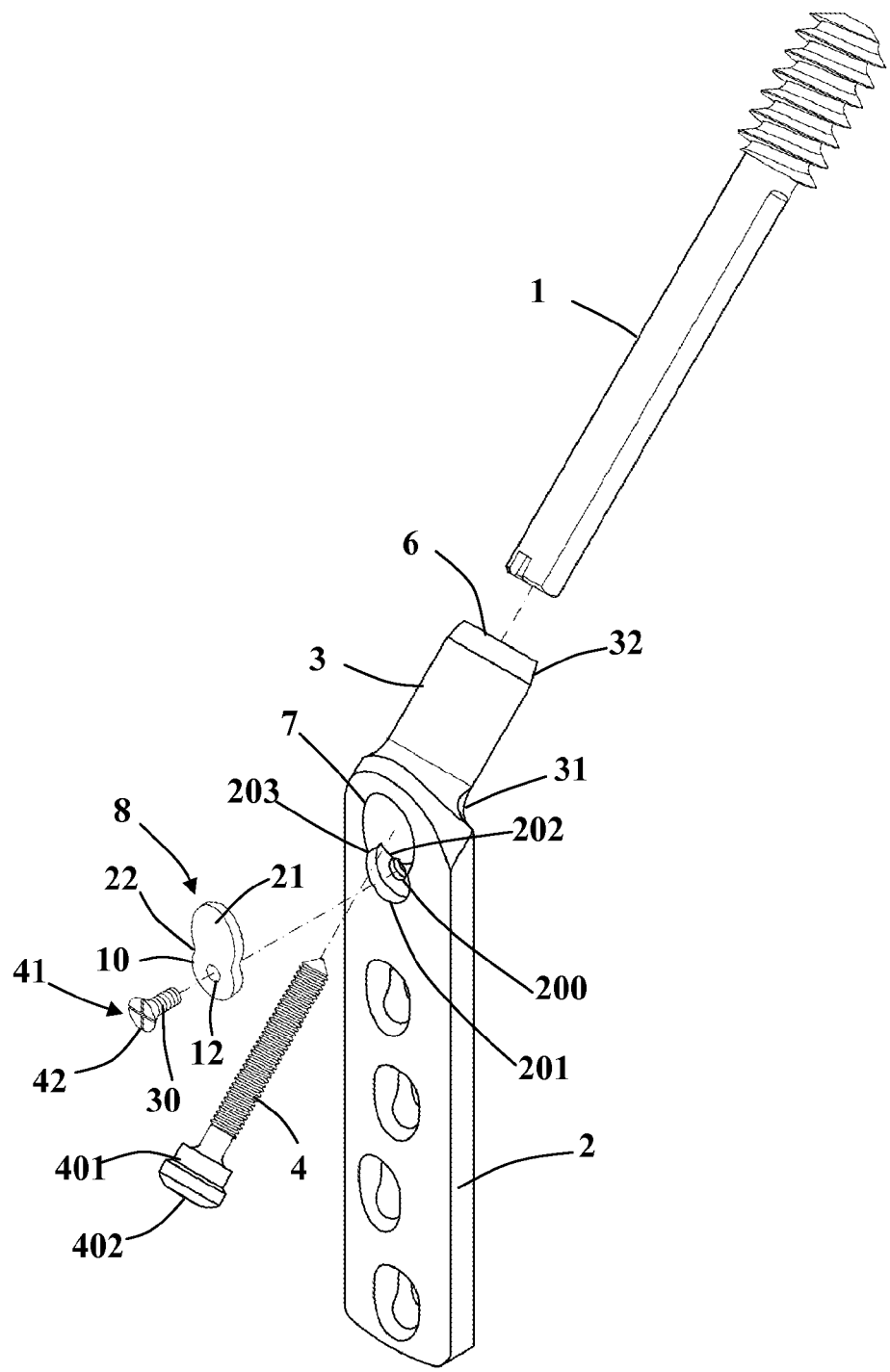
FIG. 7 is an exploded perspective view of a DHS and the rear-retaining structure of the second embodiment of the present invention.
Figure 8:
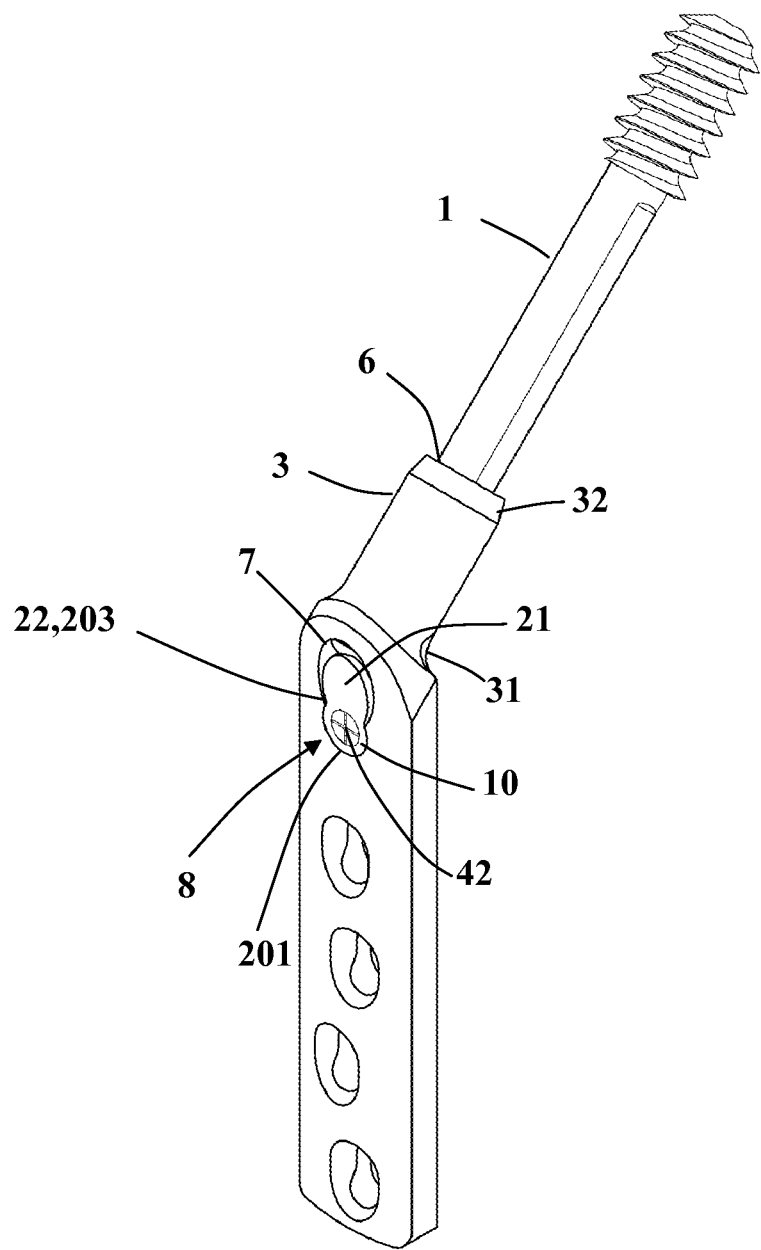
FIG. 8 is a three-dimensional view of the assembly of a DHS with the rear-retaining structure of the second embodiment of the present invention.

As showed in FIGS. 7 to 9, a part of the peripheral edge of the retaining block 10 extends upwardly to form a stopper portion 21. The retaining block 10 is fixed on the sideplate 2 by passing the screw 41 through the bore 12. The stopper portion 21 is located opposite to the lower orifice 7, and the highest point P1 of the stopper portion 21 is located above the center point P2 of the lower orifice 7. Thus, the stopper portion 21 directly contacts the compression screw 4, which keeps the lag screw 1 and compression screw 4 in the implant position, and the lag screw 1 and compression screw 4 cannot slip back out and the micor-slip distance is 0 mm. In some fracture healing cases, it is also beneficial for fracture healing to fix the lag screw 1 and compression screw 4 so that their slip back is blocked.

As showed in FIGS. 7 to 9, a container housing tank 201 is set on the surface of the sideplate 2 located below the lower orifice 7 of the sleeve 3, and a communicating part 202 is set between the lower orifice 7 and the container housing tank 201. The said fixation hole 200 is located in the slot base of the container housing tank 201. On the right and left side walls of the communicating part 202, there are at least one protrusion 203. The retaining block 10 is locked in the container housing tank 201 by the positioning element 30, and the stopper portion 21 is located opposite to the lower edge of the lower orifice 7 through the communicating part 202. At least one concave portion 22 is set at the sides of the stopper portion 21 of the retaining block 10. The retaining block 10 is locked in the container housing tank 201 by the screw 41, and the stopper portion 21 is located opposite to the lower edge of the lower orifice 7 through the communicating part 202. The protrusion 203 is embedded in the concave portion 22 to limit the rotating shift of the retaining block 10 and the stopper portion 21 around the screw 41.

In summary, whether the rear-retaining structure showed in FIGS. 3 to 5, which allows for a macro slip back, or the rear-retaining structure showed in FIGS. 7 to 9, which fixes the lag screw 1 and compression screw 4 in the implant position, should be used after the fixation of DHS by a surgical method will depend on the clinician's judgment according to the individual case of the fracture.

The invention claimed is:

1. A dynamic hip screw (DHS) with a rear-retaining structure, comprising:
   a dynamic hip screw, which comprises a lag screw, a sideplate, a sleeve, and a compression screw, wherein
      the sleeve is obliquely connected to a top end of the sideplate;
      the sleeve has an axial bore passing through a first end of the sleeve to form a lower orifice and through a second end of the sleeve to form an upper orifice;
      a lower end of the lag screw enters the sleeve from the upper orifice, and the compression screw locks into the lower end of the lag screw from the lower orifice; and
      the sideplate has a fixation hole set at a position near the lower orifice of the sleeve, and
   a rear-retaining structure, which comprises:
      a retaining block, and
      a positioning element;
   wherein the positioning element is fixed in the fixation hole; the retaining block is mounted on an outer surface of the sideplate at a position adjacent to the lower orifice of the sleeve; the retaining block has a stopper portion opposite to the lower orifice, wherein the highest point of the stopper portion is located below the center of the lower orifice, and when the compression screw is at an initial implant position with a nail head thereof pushed up against the lower orifice, a gap exists between the highest point of the stopper portion and an end surface of the nail head of the compression screw to allow the lag screw and the compression screw to slip back in the sleeve from the initial implant position toward the lower orifice; and when the dynamic hip screw is fixed in a femoral neck fracture of a proximal femur, the higher the stopper portion is in the lower orifice, the smaller the distance that the lag screw and the compression screw are allowed to slip back in the sleeve from the initial implant position toward the lower orifice.

2. The dynamic hip screw with a rear-retaining structure of claim 1, wherein the positioning element is integrally formed with the side of the retaining block.

3. The dynamic hip screw with a rear-retaining structure of claim 1, further comprising a container housing tank set on the surface of the sideplate and located below the lower orifice of the sleeve, and a communicating part set between the lower orifice and the container housing tank, wherein the fixation hole is located in a slot base of the container housing tank; the retaining block is locked in the container housing tank by the positioning element; and the stopper portion is located opposite to a lower edge of the lower orifice by passing through the communicating part.

4. The dynamic hip screw with a rear-retaining structure of claim 1, wherein when the dynamic hip screw is fixed in a femoral neck fracture of a proximal femur, the shortest distance between the highest point of the stopper portion and the end surface of the nail head of the compression screw at the implant site is 10 mm.

\* \* \* \* \*